United States Patent [19]

Priest

[11] Patent Number: 5,789,175

[45] Date of Patent: Aug. 4, 1998

[54] PRESSURE ACTUATED EXPOSURE MECHANISM FOR STERILANT INDICATOR

[75] Inventor: Robert M. Priest, Eastlake, Ohio

[73] Assignee: Steris Corporation, Mentor, Ohio

[21] Appl. No.: 905,872

[22] Filed: Aug. 4, 1997

[51] Int. Cl.⁶ ............................................. G01N 31/22
[52] U.S. Cl. ........................ 436/1; 422/58; 422/85; 422/87; 436/164; 436/169
[58] Field of Search ........................ 422/56, 58, 61, 422/85, 87, 28; 436/1, 135, 164, 169; 73/64.46, 23.27, 23.29, 712

[56] References Cited

U.S. PATENT DOCUMENTS

| | | | |
|---|---|---|---|
| 3,258,312 | 6/1966 | Olson et al. | 422/34 |
| 3,568,627 | 3/1971 | Selinger et al. | 422/57 |
| 4,145,186 | 3/1979 | Anderson | 422/57 |

*Primary Examiner*—Lyle A. Alexander
*Attorney, Agent, or Firm*—Fay, Sharpe, Beall, Fagan, Minnich & McKee

[57] ABSTRACT

A sheet of chemically sensitive paper (54) that exhibits a measurable change in a physical property, such as color, when exposed to a chemical environment is inserted between two sections (20, 22) such that an area of the paper is exposed to the chemical environment through an opening (46) in the upper section. The lower section is connected to a piston (14) that is located in a chamber (10) such that an area at the top of the chamber is sealed by the piston. The piston responds to changes in pressure by moving within the chamber. As it does so, a ratchet mechanism (30) causes the upper and lower sections to rotate one step relative to each other. With each rotational step, a new area of the chemically sensitive paper is exposed to the chemical environment through the opening in the upper section. In this manner, a record of a series of chemical exposures is obtained.

16 Claims, 1 Drawing Sheet

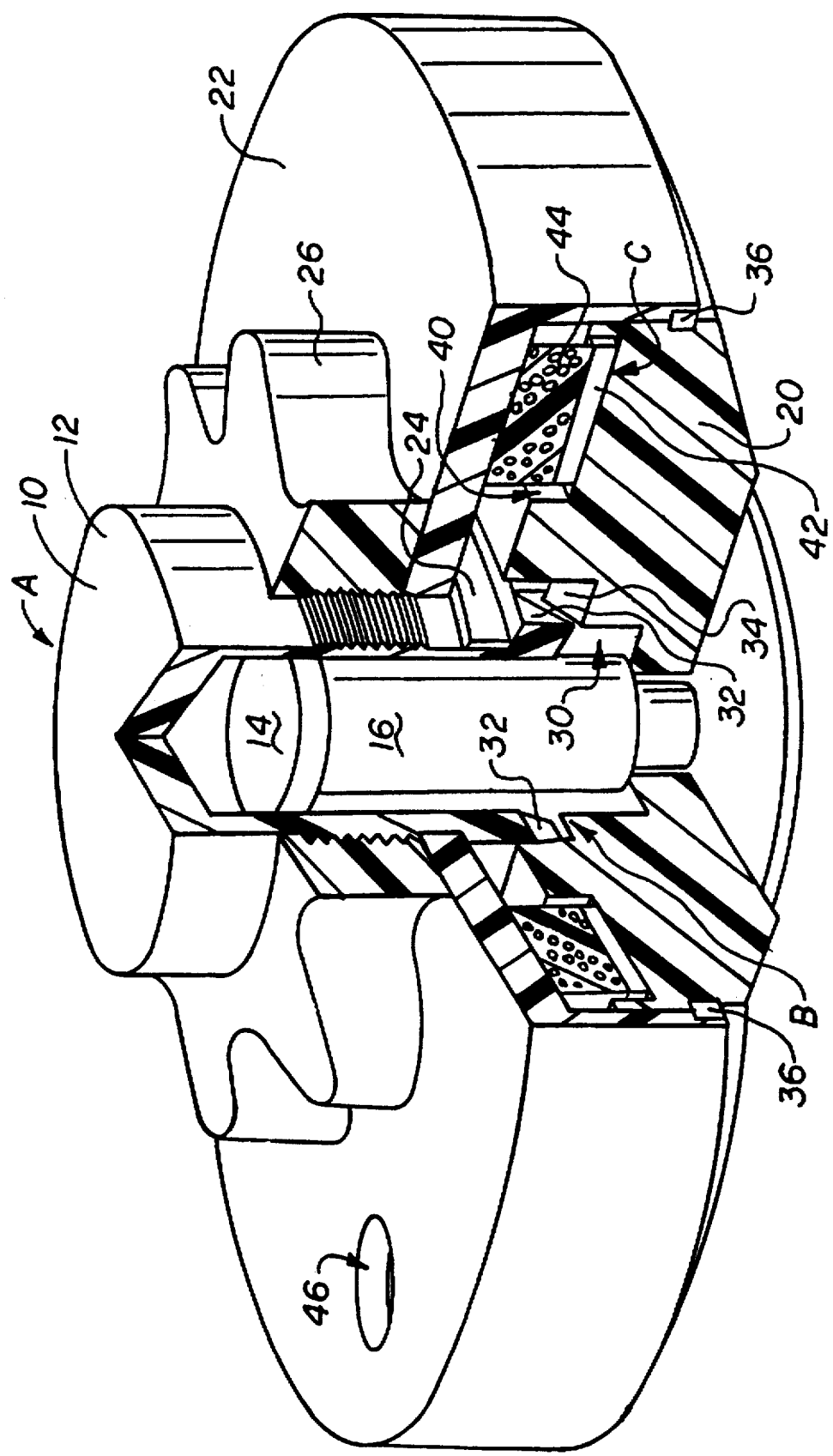

PRESSURE ACTUATED EXPOSURE MECHANISM FOR STERILANT INDICATOR

BACKGROUND OF THE INVENTION

The present invention relates to the sterilization arts. It finds particular application in conjunction with hydrogen peroxide vapor systems that employ a cycling process, each cycle including a vacuum phase and a sterilization phase. It should be appreciated, however, that the invention is also applicable to other sterilization systems and chemical treatment processes.

Hydrogen peroxide vapor is an effective sterilant for instruments. Because it can be used at low temperatures thermal degradation of the instruments is avoided. Further, it rapidly decomposes to water and oxygen which are not harmful and do not create spent sterilant disposal problems.

Hydrogen peroxide is normally mixed with water vapor. At the low temperatures employed for hydrogen peroxide vapor sterilization, the water vapor does not act as a sterilant but reduces the tendency of the hydrogen peroxide vapor to decompose explosively. The smaller water vapor molecules, however, permeate more rapidly into narrow lumens and other difficult to reach areas of instruments, reducing the effectiveness of the hydrogen peroxide vapor as a sterilant. Moreover, condensed water can act as a shield for submerged microorganisms, further limiting the effectiveness of the sterilant.

It has been shown that effective sterilization of even the most challenging instruments is achieved when the vacuum atmosphere in the sterilization chamber is cycled, with a sterilization phase followed by an evacuation phase. During the evacuation phase, water and hydrogen peroxide vapor are drawn out of the instruments. The hydrogen peroxide vapor is pulled further into the narrow lumens of the instruments in the subsequent sterilization phase as the vacuum level is lowered. As a result, complete sterilization is achieved within relatively short periods of time.

For peak effectiveness, such a sterilization system requires that a low vacuum be drawn between each of the sterilization phases and that a prescribed concentration of sterilant is achieved in each of the sterilization phases. Current methods for detecting whether the required pressures and vapor concentrations are achieved are complex and rely on expensive monitoring equipment that is unsuited to medical laboratories and the like where such sterilization equipment is predominantly used. Simpler detection devices are available for indicating that the required pressure and vapor concentration are each achieved at least once some time during the sterilization process. However, these devices are unable to show that the required conditions are achieved during each of a series of cycles.

The present invention provides a new and improved system for the detection of a series of evacuation and sterilization pulses in a sterilization process which overcomes the above referenced problems and others.

SUMMARY OF THE INVENTION

In accordance with one aspect of the present invention, a pressure actuated chemical indicator is provided for indicating multiple exposures to a sterilant vapor. An expansible element expands and contracts in response to changes in pressure in a surrounding sterilant receiving environment. A chemical integrator has physical properties which change in response to exposure to the sterilant vapor. A drive mechanism powered by the expansible element causes relative movement between the chemical integrator and a window through which a portion of the chemical integrator is exposed to the surrounding environment.

In accordance with another aspect of the present invention, a method is provided for evaluating a chemical process. The process includes a series of cycles, each cycle including drawing down pressure in the chamber and introducing a chemical in a gaseous or vaporized state which raises the pressure. A chemical indicator is placed within the process chamber. The chemical indicator includes a pressure extensible member which extends and contracts with changes in pressure in the processing chamber, a chemical integrator, and a drive mechanism powered by the expansion and contraction of the expansible member to index portions of the chemical integrator to be exposed to the processing chamber through a window. As the pressure drops, the extensible member extends; as the pressure in the processing chamber increases, the extensible member contracts. The expansion and contraction of the extensible member is converted into relative movement of the chemical integrator and the window, bringing a next region of the chemical integrator into alignment with the window to be exposed to the gaseous or vaporized chemical in the process chamber. These steps are repeated a plurality of times such that a plurality of regions of the chemical integrator are exposed to the gaseous or vaporized chemical in the process chamber. The integrator mechanism is removed from the chamber and the chemical integrator is evaluated for changes attributable to the gaseous or vaporized chemical in each of the plurality of cycles.

One advantage of the present invention is that it enables the adequacy of evacuation and vapor introduction during each of a series of evacuation and sterilization cycles to be monitored.

Another advantage is that the device is reusable for subsequent sterilization processes.

Another advantage is that devices embodying the invention are relatively inexpensive to manufacture and use.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

The FIGURE is a cut-away drawing of a preferred embodiment of a pressure actuated for chemical indicators in accordance with the present invention.

DETAILED DESCRIPTION OF THE PREFERRED EMBODIMENTS

With reference to the FIGURE, a pressure actuated exposure mechanism for chemical indicators includes an expense vault element A which expands and contracts with increases and decreases in pressure. The expansible element is connected with a mechanical drive B which converts the expansion and contraction of the expansible element into mechanical movement which indexes a chemical indicator C into and out of a position in which is exposed to the atmosphere surrounding the mechanism.

The expansible element A includes a housing 10 finding an interior chamber 12 in which a piston 14 is slidably disposed. The piston is slidably connected with interior walls of the housing 12 in a pressure sealing relationship such that changes in the relative pressure between the interior 12 of the housing and the exterior of the housing cause the piston to move upward and downward. In the preferred embodiment in which the vacuum to be measured is about 0.5 Torr or less, the chamber 12 is initially charged with a sub-atmospheric pressure. The pressure of the initial charge like the diameter of the piston and the height of the housing are selected such that the piston travels a preselected distance, when the external pressure varies between the minimum acceptable high and low pressures encountered in the sterilization cycle to be monitored. In the preferred embodiment, the piston 14 is intricately formed with a shaft 16 which extends from the housing 10 to facilitate interconnection with the drive mechanism B. Optionally, the chamber 12 may contain a sealed pouch or bellows arrangement to assure that the pressure in the chamber 12 does not vary due to leakage around the piston 14.

In the preferred embodiment, the drive mechanism causes an annular carrier element 20 to (1) rotate circumferentially around the housing 10 and (2) move parallel (vertically) to the piston 14. More specifically, each time the ambient pressure increases relative to the pressure in the chamber 12, the carrier member 20 moves upward relative to an upper fixed housing portion or cover 22 to lock an annular strip of the chemical indicator C between itself and the upper cover 22. Each time the ambient pressure around the mechanism decreases relative to the chamber 12, the carrier element 20 moves downward, releasing the mechanical lock, and rotates or indexes. The annular cover 22 is supported by a ledge 24 on the upper housing 10 against which it is locked by a threaded locking nut 26.

In the illustrated embodiment, the piston shaft 16 is connected with the annular carrier 20 such that the two move up and down together relative to the cover portion 22. The rotary movement in the preferred embodiment comes from a ratchet mechanism 30 mounted between the cover 22 or elements mounted stationarily thereto and the annular carrier member 20 or elements mounted stationarily thereto.

A ratchet mechanism 30 such as upper teeth 32 and lower teeth 34 are mounted between the stationary and moving structures. The interacting teeth 32, 34 can be formed in any adjoining rotating/stationary surfaces that are convenient. As the upper and lower teeth move towards each other, their angled, camming surfaces interact forcing the annular carrier 20 and the cover 22 to rotate relative to each other. The vertical surfaces of at least one set of teeth are slightly undercut. The teeth are sufficiently resilient that the teeth snap past each other as the teeth pull apart shifting the aligned cammed surfaces to the next tooth. Preferably, a one-way mechanism 36 assures that the annular carrier and housing only rotate in single direction relative to each other and cannot inadvertently kick back. Again, the one-way mechanism may be located between any of the surfaces which rotate relative to each other as may be convenient for molding purposes. The height of the teeth 32, 34 are selected to be just slightly shorter than the travel of the piston 14 such that the teeth move sufficiently out of engagement to permit indexing to the next tooth. The width of each tooth determines the distance of relative rotation and the angle of the cammed surface determines the mechanical advantage.

In the preferred embodiment, the annular carrier 22 defines an angular groove 40 within which the chemical indicator C is received in the form of the annular strip 42. A resilient gasket 44 is affixed to the cover 22 extending into the groove 40. The upper housing or cover 22 and the gasket 44 have an aperture 46 defined therein. The width of the aperture 46 and the circumferential dimension are selected relative to the amount of rotation which the drive mechanism B generates per cycle. In the preferred embodiment, each cycle brings a previously unused section of the chemical indicator strip 42 into alignment with the aperture 46. Of course, a slight amount of overlap is permitted. The sealing gasket 44 surrounding the aperture 46 and engages the indicator strip 42 with sufficient sealing force that hydrogen peroxide vapor is prevented from flowing beyond the aperture 46 along the underside of the gasket.

To examine the chemical indicator strip after a sterilization cycle and to replace it for the next cycle, the nut 26 is unthreaded from the housing 10. The cover 22 is lifted off exposing the chemical indicator strip 42 for easy examination and replacement.

In preparation for use, a new chemical indicator disk 42 is placed in the groove 40 and the cover 22 is clamped in place with the nut 26. The mechanism is then placed in a sterilizer chamber along with articles to be sterilized. The sterilization chamber is initially evacuated to a selected low pressure typically in the range of 0.1 to 0.5 Torr. The initial evacuation removes water and other vaporizable liquids from the items to be sterilized. Under the low pressure in the sterilization chamber, the piston is pushed downward by the higher pressure in the chamber 12 causing the shaft 16 to extend. This moves the annular carrier 20 downward. The gasket 44 expands maintaining a vapor tight relationship with the carrier strip 42 until the pressure in the sterilization chamber is sufficiently low that the vapor concentration is below the activation threshold of the carrier strip.

Once the low vacuum is stabilized indicating the removal of vaporizable liquids, a sterilant vapor, e.g., hydrogen peroxide vapor, is injected into the sterilization chamber. The injection of this vapor gradually raises the pressure in the sterilization chamber, e.g., to about 70–100 Torr. As the pressure begins to increase, the piston 14 pulls upward and the shaft 16 retracts pulling the cover 22 and carrier element 20 together. As the cover and carrier element move together, the cam surfaces of the ratchet teeth 32, 34 engage causing relative rotation of the housing and cover. The indicator strip 42 rotates with the carrier element moving a new section into alignment with the aperture 46. The gasket 44 regains its vapor tight relationship with the carrier strip 42. The higher vapor pressure is maintained for a preselected duration permitting the sterilant vapor to contact the items to be sterilized. After this preselect duration, the sterilization chamber is again pumped to the lower vacuum exhausting the sterilant and other vapors. The lower vacuum also causes the piston 14 to move down and the shaft 16 to extend cocking the mechanism in preparation for the next sterilization cycle. When the sterilant vapor is next injected into the sterilization chamber, the increase in pressure again causes the next section of the chemical indicator strip to be indexed into alignment with the aperture 46. Typical sterilization processes involve 3 to 10 of such evacuation and sterilant vapor injection cycles. After the sterilization process is complete and the sterilization chamber is exhausted, the mechanism is removed along with the sterilized articles. The nut 26 and cover 22 are removed to expose the indicator disk 42. If each evacuation and sterilant injection cycle incurred properly, the chemical indicator disk will have a series of spots each of the same color and spacing indicating that an appropriate amount of sterilant was injected in each cycle and that a sufficient vacuum was drawn between each sterilant vapor injection. A failure to index causes the same spot to be exposed twice leaving the number of spots short by one, and the length of the carrier strip 42 between first and last spots shorter than expected. Similarly, insufficient sterilant in a sterilization cycle causes a missing spot and a larger than expected spacing between the adjoining spots. Optionally, the chemical indicator can be formulated such that exposure to the sterilant vapor for the selected duration causes a first readily perceivable color change and exposure for a second period causes a further readily distinguishable color change. With an indicator so formulated, variations in the color of the spots are indicative of variations in sterilant vapor concentration in the cycles.

Various alternate embodiments will immediately present themselves to those of ordinary skill in the art. As one example, the ratch mechanism can be placed between other structures that rotate with the cover and the carrier. As another, the aperture 46 may be moved to the overhanging flange of the cover member 22 and a band of the chemical indicator material placed between the support member 20 and the vertical flange of the cover member. Of course, in such a mechanism the vertical movement of the support member 20 is not necessary and can be eliminated. Analogously, other types of mechanical motion rather than rotation are contemplated. For example, the extensible element A may be used to drive a linear system. As another example, the extensible element can be used to index cogs or pulleys on which a band of the chemical indicator material is supported.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A pressure actuated device for indication of a gaseous or vaporized sterilant comprising:

(a) a chamber including a top and a cylindrical side, the cylindrical side having an outer surface and an inner surface;

(b) a piston disposed within the chamber such that the top the inner surface of the side, and the piston enclose a sealed, expansible space within the chamber, the piston responding to differences in pressure between a pressure in the expansible space within the chamber and external pressure by moving upward when the external pressure is higher and downward when the external pressure is reduced;

(c) an upper element including a cover and a cylindrical side subtending from an outer edge of the cover, the cover including an upper and a lower surface and a central opening wide enough to enable the upper element to fit over the chamber and slide vertically against the cylindrical side of the chamber, and a second opening;

(d) a lower carrier element including a top surface, a cylindrical side subtending from the top surface of the lower element, and a base, the cylindrical side of the upper element and the cylindrical side of the lower element slidingly engaged, and the top surface of the lower element being disposed in a facing relation to the lower surface of the cover, the top surface including a central opening, the base being connected to a base portion of the piston such the lower element moves vertically as the piston moves correspondingly;

(e) a ratch drive for causing relative rotation between the cover and the lower carrier element in response to vertical movement of the piston in the chamber, a first portion of the ratch drive being connected with one of the piston and the lower carrier element and a second portion of the ratch drive being connected with one of the cover and the cylindrical side of the chamber; and, (f) a sheet of indicator paper, the paper including a substance that exhibits a measurable change in a property in response to the sterilant, the indicator being positioned between the lower surface of the cover and the top surface of the lower carrier element, the lower element and the cover interacting to prevent free sterilant penetration of the indicator paper such that an area of the indicator paper is exposed through the second opening in the cover.

2. The device of claim 1, wherein the top surface of the lower element includes a circular groove, situated equidistant from the central opening in the lower element, the groove receiving a gasket for sealing engagement with portions of the indicator paper not aligned with the cover second opening.

3. The device of claim 1, further including a nut with an inner thread which engages a corresponding thread on the outer surface of the chamber side for holding the cover in a fixed relationship to the chamber.

4. The device of claim 1, wherein the mechanism is constructed of materials that are resistant to degradation by hydrogen peroxide vapor and low vacuum, and wherein the indicator paper contains a chemical with a measurable physical property that changes in relation to the level of exposure of the indicator paper to hydrogen peroxide.

5. The device of claim 1 wherein the space is maintained at a low pressure such that subjecting the device to pressures close to atmospheric pressure causes the piston to rise in the chamber, drawing the lower element up towards the cover and thereby sealing the indicator paper against the cover.

6. The device of claim 1 wherein the space is maintained at a preselected low pressure such that the piston is not drawn down in the chamber until the external pressure is reduced below that in the space, thereby enabling the device to detect whether a sufficient vacuum has been drawn.

7. A pressure actuated device for indication of multiple exposures to a gaseous or vaporized sterilant, the device comprising:

an expansible element which expands and contracts in response to changes in pressure in a surrounding sterilant receiving environment;

a chemical indicator whose physical properties change in response to exposures to the sterilant and is capable of multiple discrete exposures to the sterilant;

a drive mechanism powered by the expansible element to cause relative movement between the chemical indicator and a window through which a portion of the chemical indicator is exposed to the surrounding environment.

8. The device of claim 7 wherein the expansible element includes a sealed chamber within which a piston is slidably mounted, such that changes in pressure in the surrounding environment relative to pressure in the chamber cause the piston to shift.

9. The device of claim 7 wherein the pressure in the surrounding environment cycles between a pre-selected upper pressure and a pre-selected lower pressure and wherein the drive mechanism includes:

a ratchet mechanism which steps in response to the pressure of the surrounding environment cycling between the pre-selected upper and lower pressures, whereby the chemical indicator and window are moved relative to each other in steps in accordance with the cycling pressure in the surrounding environment.

10. The device of claim 7 further including:

an annular carrier which carries the chemical indicator along an upper annular surface thereof, the annular carrier being mounted for rotation around the expansible element;

the window being defined in an annular upper cover which extends around the expansible element and covers the chemical indicator; and the drive mechanism rotating the annular carrier and the upper cover relative to each other to index different sections of the chemical indicator into alignment with the window.

11. The device of claim 10 wherein the drive mechanism further moves the cover and the annular carrier toward and away from each other such that sections of the chemical indicator disposed adjacent the window are clamped firmly between the annular carrier and the cover.

12. The device of claim 11 further including a resilient gasket disposed between the cover and the annular carrier for resiliently sealing portions of the chemical indicator displaced from the window from being contacted by the sterilant vapor.

13. A method for evaluating a chemical process, the process including a series of cycles, each cycle including drawing down pressure in a process chamber and introducing a chemical sterilant in a gaseous or vaporized state which raises the pressure, the method comprising:

(a) placing a device within the process chamber, which device includes a pressure extensible member which extends and contracts with changes in pressure in the process chamber, a chemical indicator, and a drive mechanism powered by expansion and contraction of the expansible member to index portions of the chemical indicator to be exposed to the sterilant only through a window;

(b) as the pressure in the process chamber drops, extending the extensible member and as the pressure in the process chamber increases, contracting the extensible member;

(c) converting the expansion and contraction of the extensible member into relative movement of the chemical indicator and the window bringing a next region of the chemical indicator into alignment with the window to be exposed to the gaseous or vaporized chemical sterilant in the process chamber;

(d) repeating steps (b) and (c) a plurality of times such that a plurality of regions of the chemical indicator are exposed to the gaseous or vaporized chemical sterilant in the process chamber;

(e) removing the device from the process chamber and evaluating the chemical indicator for changes attributable to the gaseous or vaporized chemical sterilant in each of the plurality of cycles.

14. The method set forth in claim 13, wherein step (c) includes rotating the chemical indicator beneath the window.

15. A method for evaluating a chemical process, the process including a series of cycles, each cycle including drawing down pressure in a process chamber and introducing a sterilizing chemical in a gaseous or vaporized state which raises the pressure, the method comprising:

(a) inserting a piece of chemical indicator paper in a pressure actuated exposure mechanism, the indicator paper including a substance that exhibits a measurable change in a property when subjected to the chemical process, the mechanism including an upper element, a lower element, and a means for rotating the lower element in relation to the upper element in response to selected changes in pressure, the upper element including an opening through which the indicator paper is exposed to the chemical environment, such that a new area of paper is exposed to the environment when the lower element rotates relative to the upper element;

(b) subjecting the pressure actuated exposure mechanism to the chemical process;

(c) removing the indicator paper from the mechanism; and (d) evaluating the indicator paper to determine the level of exposure to the chemical in a plurality of the chemical process cycles.

16. The method of claim 15, wherein the chemical is hydrogen peroxide vapor.

* * * * *